US012625136B2

(12) United States Patent
Van Roy et al.

(10) Patent No.: US 12,625,136 B2
(45) Date of Patent: May 12, 2026

(54) SENSOR DEVICE

(71) Applicant: Imec vzw, Leuven (BE)

(72) Inventors: Willem Van Roy, Bierbeek (BE); Tim Stakenborg, Heverlee (BE); Kris Covens, Kessel-Lo (BE)

(73) Assignee: Imec vzw, Leuven (BE)

( * ) Notice: Subject to any disclaimer, the term of this patent is extended or adjusted under 35 U.S.C. 154(b) by 1031 days.

(21) Appl. No.: 17/540,551

(22) Filed: Dec. 2, 2021

(65) Prior Publication Data

US 2022/0091117 A1 Mar. 24, 2022

Related U.S. Application Data

(62) Division of application No. 15/577,076, filed as application No. PCT/EP2016/065449 on Jun. 30, 2016, now abandoned.

(30) Foreign Application Priority Data

Jun. 30, 2015 (EP) ..................................... 15174417

(51) Int. Cl.
| | |
|---|---|
| *G01N 33/543* | (2006.01) |
| *C12Q 1/00* | (2006.01) |
| *C12Q 1/6825* | (2018.01) |
| *G01N 33/52* | (2006.01) |

(52) U.S. Cl.
CPC ....... *G01N 33/54393* (2013.01); *C12Q 1/002* (2013.01); *C12Q 1/6825* (2013.01); *G01N 33/523* (2013.01)

(58) Field of Classification Search
None
See application file for complete search history.

(56) References Cited

U.S. PATENT DOCUMENTS

| | | | | |
|---|---|---|---|---|
| 4,356,863 | A | 11/1982 | Furr | |
| 6,284,117 | B1 * | 9/2001 | Smolko | ............... B01D 63/068 |
| | | | | 210/321.89 |
| 6,300,141 | B1 | 10/2001 | Segal et al. | |
| 2003/0186327 | A1 * | 10/2003 | Babcook | ............ G01N 33/6854 |
| | | | | 435/7.1 |

(Continued)

FOREIGN PATENT DOCUMENTS

| | | |
|---|---|---|
| CN | 102112877 A | 6/2011 |
| CN | 102159303 A | 8/2011 |

(Continued)

OTHER PUBLICATIONS

PCT International Search Report and Written Opinion, PCT International Application No. PCT/EP2016/065449, dated Oct. 11, 2016, 13 pages.

(Continued)

*Primary Examiner* — Matthew D Krcha
(74) *Attorney, Agent, or Firm* — McDonnell Boehnen Hulbert & Berghoff LLP

(57) ABSTRACT

A device (1) for sensing an analyte, the device (1) comprises at least a sample inlet (10) for receiving a sample, affinity probes (111) selected to have a preferential binding to the analyte, a transducer (11) sensitive to a characteristic of the analyte and/or a label attached to the analyte, the transducer not being a FET transducer, and a desalting unit (13) for desalting the received sample.

12 Claims, 6 Drawing Sheets

(56)                    References Cited

U.S. PATENT DOCUMENTS

| | | | |
|---|---|---|---|
| 2004/0146937 A1* | 7/2004 | Rich .................. | G01N 33/6803 |
| | | | 435/7.1 |
| 2006/0205061 A1 | 9/2006 | Roukes | |
| 2007/0116607 A1 | 5/2007 | Wang et al. | |
| 2016/0046988 A1* | 2/2016 | Walter ................. | C12Q 1/6837 |
| | | | 422/69 |

FOREIGN PATENT DOCUMENTS

| | | | | |
|---|---|---|---|---|
| JP | 2002-536962 A | 11/2002 | | |
| JP | 2005-513441 A | 5/2005 | | |
| JP | 2007-178437 A | 7/2007 | | |
| JP | 2008-107245 A | 5/2008 | | |
| JP | 2009-236933 A | 10/2009 | | |
| JP | 2012-254452 A | 12/2012 | | |
| JP | 2013-515260 A | 5/2013 | | |
| WO | 99/33559 A1 | 7/1999 | | |
| WO | WO-0037163 A1 * | 6/2000 | ............ | B01D 57/02 |
| WO | 2003/019164 A1 | 3/2003 | | |
| WO | 2004/038363 A1 | 5/2004 | | |
| WO | 2009/141637 A1 | 11/2009 | | |
| WO | 2010/011760 A1 | 1/2010 | | |
| WO | 2011/078777 A1 | 6/2011 | | |
| WO | 2014/062799 A1 | 4/2014 | | |
| WO | 2014/069551 A1 | 5/2014 | | |

OTHER PUBLICATIONS

Sabate Del Rio, Jonathan et al., "Real-Time and Label-Free Ring-Resonator Monitoring of Solid-Phase Recombinase Polymerase Amplification", Biosensors and Bioelectronics, vol. 73, 2015, pp. 130-137.

Swaminathan, Vikhram Vilasur et al., "Electronic Desalting for Controlling the Ionic Environment in Droplet-Based Biosensing Platforms", Applied Physics Letters, vol. 106, 2015, pp. 053105-1-053105-5.

Abbott 2008 Learning Guide Immunoassay, Abbott Laboratories, pp. 1-44.

Carrara, S., Bio/CMOS Interfaces and Co-Design Book, Faculties Sciences et Techniques de l'Ingénieur and Informatique et Communications Labo. Systèmes Intégrés (LSI), Lausanne, Switzerland, 2012, pp. 1-266.

Chin, C.D., et al., "Commercialization of Microfluidic Point-of-Care Diagnostic Devices", Lab Chip, 2012, vol. 12, pp. 2118-2134.

* cited by examiner

SENSOR DEVICE

The present application is a divisional of U.S. application Ser. No. 15/577,076, filed Nov. 27, 2017, which is a section 371 U.S. patent application claiming priority to PCT/EP2016/065449, filed Jun. 30, 2016, which claims priority from EP Application Serial No. 15174417.4, filed Jun. 30, 2015, the contents of these applications which are hereby incorporated by reference.

TECHNICAL FIELD OF THE INVENTION

The present invention relates to a device for sensing an analyte and to a method for measuring the presence and/or concentration of an analyte in a sample. In particular embodiments, the present invention may relate to a biosensor device.

BACKGROUND OF THE INVENTION

Affinity-based sensors are devices for sensing and detecting analytes in a sample, for instance in a liquid sample. Such sensors may operate on the basis of electrical, electrochemical, chemical, optical, magnetic, electromagnetic, mechanical, and/or acoustic detection principles. The detection of analytes in the sample is performed through interaction and reaction between specified reactants and the analytes in the sample. In particular in an affinity-based biosensor, the detection is based on the formation of a complex (hybridisation) between at least two entities, i.e. the analyte and a receptor or capture probe which may be immobilized on or in a substrate. The complex formation between the analyte and the capture probe leads to a signal that is measurable by a signal measurement unit. In order to make the binding detectable, in particular embodiments, a label element may be attached to the analyte. In alternative embodiments, however, detection may be based on a label-free operation.

Real time sensing of biomolecules as a particular type of analytes, is particularly useful in many applications such as disease diagnosis or food safety, for example. Unfortunately, the response time of a biosensor device is often slow. This response time depends on a huge number of parameters such as, among other, the concentration of the analyte, the diffusion of the analyte, the kinetics of the hybridisation reaction and the stability of the obtained complex. For biosensors, the response times can vary from a few seconds to hours or more. It is generally admitted that in point-of-care (POC) or point-of-need applications, response time must be no longer than about 10 minutes. Moreover, the Limits of Detection (LOD) of existing biosensors can become higher (worse) if the various incubation times are reduced below their recommended values.

There is therefore still a need to dispose of a device having short response time in the detection of the presence and/or in the measurement of concentrations of analyte and, preferably, having low limit of detection values. Furthermore, the methods implemented at present in devices for sensing an analyte, for instance in biosensors, need to be improved in order to decrease the response time.

SUMMARY OF THE INVENTION

It is an object of embodiments of the present invention to provide a device for sensing an analyte, for instance a biosensor, having a rapid response time for the detection of the presence and/or for the determination of the concentration of the analyte in a sample. Alternatively or additionally, the device according to embodiments of the present invention may present an increased signal of the transducer, thereby allowing to detect the analyte more rapidly and/or at smaller concentrations.

It is also an object of the present invention to provide a method to be implemented in a device for measuring an analyte, for instance in a biosensor, the method leading to fast response times for the detection of the presence and/or for the determination of the concentration of the analyte in a sample.

In a first aspect, the present invention relates to a device for sensing an analyte, for instance a biosensor, the device comprising at least a sample inlet for receiving a sample, in particular for instance a liquid sample, affinity probes selected to have a preferential binding to the analyte, and a transducer sensitive to a characteristic of the analyte and/or a label attached to the analyte, and adapted to convert an interaction of the analyte with the affinity probes into a readout signal, the transducer not being a field-effect transducer, such as a field-effect transistor (FET), and a desalting unit for desalting the received sample so as to increase the binding rate between the affinity probes and the analyte and consequently to reduce the response time and/or increase the signal of the transducer.

The inventors have surprisingly found that the presence of a desalting unit in a device for sensing an analyte, for instance a biosensor, permits to obtain a faster response from the device. The measurable signal (the output signal) increases faster as compared to a similar device without the desalting unit. Moreover, by using a desalting unit in a device for sensing an analyte, the limit of detection is decreased (=improved).

The desalting unit may be any of a dilution means, a concentration/redispersion means, an electrodialysis means, or any other suitable means.

By the term "dilution means", is meant a means suitable to decrease the ionic strength of the sample containing the analyte by dilution with a fluid, for instance a buffer fluid. The fluid may be a solution having a lower ionic strength than the ionic strength of the provided sample. In particular embodiments, the dilution means comprises a mixer and/or a fluid reservoir, for instance a buffer fluid reservoir. The use of a dilution means has the advantage that it is easy to implement and fast in operation, thus allowing a short sample-to-answer time, but it has the disadvantage that not only the ionic strength of the sample is reduced, but that also the analyte concentration is reduced. Nevertheless, the overall performance of the sensor device is improved.

By the term "concentration/redispersion means", an analyte concentrator coupled to a redispersion means is meant. By using the analyte concentrator, analyte is brought into a more concentrated state. The redispersion means is suitable to redisperse the concentrated analyte in a solution having an ionic strength lower than the initial state (e.g. lower than physiological ionic strength if the sample was a physiological sample). In particular embodiments, the analyte concentrator may be a centrifuge, a filter (such as a paper filter, a micropillar filter, a bead filter), or a microsieve. The redispersion means may be selected from the group consisting of magnetic stirrer, mechanical stirrer, ultrasonic stirrer, flow-through device, or microfluidic device. An advantage of using a combined concentration/redispersion means is that it permits to reduce the ionic strength while the concentration of the analyte remains unaffected, if the amount of liquid added during redispersion is equal to the amount of liquid removed during concentration. The concentration of the analyte can also be increased or decreased, if desired, by adding a different volume during redispersion compared to the volume that was removed in the concentration step.

By the term "electrodialysis means", is meant a means comprising at least two ion-selective membranes (also known as ion exchange membranes) suitable for performing electrodyalisis. By the term "ion-selective", is meant that the membrane is permeable to some ions (e.g. in a cation-selective membrane: to cations such as, among other, $Li^+$, $Na^+$, $K^+$, $Ca^{2+}$ and $Mg^{2+}$, preferably $Na^+$), and not to others (e.g. in a cation-selective membrane: anions such as, among others, $F^-$, $Cl^-$, $Br^-$ and $HCO_3^-$, preferably $Cl^-$), through channels across the membrane (e.g. pores or holes). The ion-selective membranes are selected so as to be not permeable to the analyte. The electrodialysis means comprises electrodes on the side of the membranes opposite to the one in contact with the sample containing the analyte to be detected and/or measured. The electrodes may be actuated so as to attract the cations, for instance $Na^+$, and more preferably more cations, through the $Na^+$-selective or cation-selective membrane, and to attract the anions, for instance $Cl^-$, and more preferably more anions, through the $Cl^-$-selective or anion-selective membrane. An advantage of an electrodialysis means is that it permits to reduce the ionic strength without diluting the analyte concentration in the sample.

It is an advantage of embodiments of the present invention that a biosensor is provided which can be used for sensing biological samples. Such biological samples may for instance be received, e.g. taken, from a patient, for instance a blood or plasma sample, a saliva sample, a urine sample, etc. Embodiments of the present invention are particularly well-suited for detection of biological targets. A biosensor device in accordance with embodiments of the present invention is a sensor, adapted for sensing the presence/absence and/or the concentration of the analyte. The medium in which the sample is received is an aqueous medium, and may contain dissolved salts, e.g. at physiological conditions (ionic strength ~150 mM).

In embodiments of the present invention, the desalting unit is internal to the sensor device, e.g. integrated on a same substrate, e.g. semiconductor substrate, or in a same enclosure as the transducer. In alternative embodiments, the desalting unit is external to the sensor device, e.g. not integrated on a same substrate or in a same enclosure as the transducer.

In embodiments, the desalting unit may furthermore comprise a port for receiving a buffer fluid for being flown to the received sample.

In embodiments of the present invention, the desalting unit may comprise a buffer fluid reservoir for containing buffer fluid. The buffer fluid reservoir may be part of the desalting unit, or may be the desalting unit as such (i.e. the desalting unit consists of the buffer fluid reservoir). In particular embodiments, the buffer fluid reservoir may be selected from the group consisting of an ampoule, a syringe, a blister, a well, a tube connecting two liquid reservoirs, an Eppendorf tube, a channel, and an on-board reservoir provided on or in a chip, being for instance a semiconductor chip or a microfluidics chip. It is advantageous to use a blister pack, a channel, or an on-chip reservoir, as the blister pack, the channel, or the on-chip reservoir is easy to be incorporated.

In alternative embodiments of the present invention, a buffer fluid reservoir for containing buffer fluid may be located outside the desalting unit.

In embodiments of the present invention, the sample inlet and the desalting unit are connected to each other by a transferring means suitable for the transfer of a sample from the sample inlet to the desalting unit.

In embodiments of the present invention, the desalting unit and the transducer are connected to each other by a transferring means suitable for the transfer of a desalted sample from the desalting unit to the transducer.

In embodiments of the present invention, an outlet port may be provided for evacuating excess sample and/or waste. On top thereof or alternatively, an internal reservoir may be provided for storing excess sample and/or waste. The outlet port and/or the internal reservoir may be connected to other parts of the sensor device by suitable transferring means.

In embodiments of the present invention, the transferring means is or are based on capillary flow. In embodiments of the present invention, the transferring means is or are based on capillary flow in an open channel. In alternative embodiments of the present invention, the transferring means is or are based on capillary flow in a closed channel. In embodiments of the present invention, the desalting unit comprises a mixer for mixing the received sample with buffer fluid. In particular embodiments, the mixer may be selected from the group consisting of a microfluidic mixer, a vortex mixer, a shaker, a magnetic mixer, an ultrasonic mixer, mechanical mixer and rapid-mixing apparatus. The rapid mixing-apparatus may comprise two syringes, one for the delivery of a sample through the sample inlet and one for the delivery of a buffer fluid through a buffer fluid inlet and a mixing chamber. In particularly advantageous embodiments, the mixer for mixing received sample with buffer fluid is a microfluidic mixer, the advantage of the microfluidic mixer being that the mixer has no moving parts.

In embodiments of the present invention, the transducer may be an optical transducer, i.e. a transducer that converts an optical signal into an electronic signal. The optical signal may be any suitable type of optical signal, such as for instance a variation of fluorescence or of refractive index or of colour.

In embodiments of the present invention, the desalting unit may be located on a same substrate or in a same enclosure as the transducer. The desalting unit may comprise the port for receiving the buffer fluid for being flown to the received sample, the buffer fluid reservoir and the mixer.

In a second aspect, the present invention provides a diagnostic device comprising a biosensor device according to embodiments of the first aspect of the present invention, for sensing an analyte and generating a sensing signal, and an output unit for providing an output of said biosensor device which can be used, alone or in combination with other factors, for basing a diagnosis on. The output unit is a device that may be adapted for outputting a signal representative for presence/absence or concentration of the analyte. Such diagnostic device is intended for use in diagnosis of disease or other conditions, including a determination of the state of health, in order to cure, mitigate, treat or prevent disease or its sequelae. Such diagnostic device or parts thereof are intended for use in the collection, preparation and examination of samples taken from a human or animal body.

In a third aspect, embodiments of the present invention relate to a method for measuring the concentration of an analyte, typically for instance a biomolecule, a protein, an antibody, an antigen, a biomarker, a cytokine, a nucleic acid, a small molecule (a small molecule typically having a molecular weight lower than a few kiloDaltons, for instance lower than 10 kDa, e.g. lower than 5 kDa, e.g. lower than 2 kDa, such as for instance between 50 Da and 1 kDa), or a metabolite, in a sample, the method comprising:

i. Obtaining or receiving a sample, e.g. a biological sample, ii. desalting the sample, thereby obtaining a desalted sample, iii. measuring at least one signal of the desalted sample by means of an affinity-based sensing device based on affinity probes and a transducer, the transducer not being a FET-transducer, iv. determining the presence and/or concentration of the analyte in the sample using the at least one signal.

By the expression "desalting the sample" is meant obtaining a decrease of the ionic strength of the sample, for example a sample in an aqueous medium with physiological salt concentration. The obtained desalted sample of step ii. has an ionic strength lower than the ionic strength of the original sample, e.g. lower than physiological ionic strength in case of a physiological sample. However, the ionic strength does not necessarily need to be zero.

The inventors have surprisingly found that thanks to the method according to embodiments of the present invention, the response time may be decreased to only a few minutes (e.g. 20 minutes or less, for instance 10 minutes or less, preferably to 5 minutes or less, more preferably to 1 minute or less) and even to only a few seconds (e.g. to 30 seconds or less, preferably to 20 seconds or less, more preferably to 10 seconds or less). This is particularly advantageous for use of a sensor in POC applications.

In embodiments of the present invention, the step ii. of desalting the sample comprises, consists essentially of, or consists of, a step of bringing the sample to an ionic strength ranging from 10 nM to 150 mM, preferably from 1 mM to 150 mM, more preferably from 10 mM to 150 mM.

In embodiments of the present invention, the step ii. of desalting the sample and the step iii. for measuring the at least one signal of the desalted sample may be performed successively. In particular embodiments the sample is first desalted and then applied on affinity probes and a transducer. In alternative embodiments, the sample is desalted on the affinity probes and the transducer, but before the measurement is started.

In alternative embodiments of the present invention, the step ii. of desalting the sample (e.g. biological sample) and the step iii. for measuring the at least one signal of the desalted sample may be performed simultaneously. In other words, in this embodiment the sample is desalted on the affinity probes and the transducer during the measurement.

In embodiments, the method according to the invention may furthermore comprise a step of comparing the at least one signal to a reference signal obtained with a standard solution. By the expression "standard solution" is meant a sample in which no analyte is present, or in which a known concentration of analyte is present.

In embodiments of the present invention, the step iii. of measuring the at least one signal of the desalted sample may be repeated over time, thus obtaining a measurement curve. In particular embodiments, the step iii. of measuring the at least one signal of the desalted sample comprises a step of determining a slope of the measurement curve. In this embodiment, the measurement is performed before a stable situation is reached.

In embodiments of the present invention, the step ii of desalting the sample comprises, preferably consists essentially of, more preferably consists of, a step of diluting the sample. The step of diluting of the sample is a simple and fast step; nevertheless the diluting leads also to the diluting of the analyte. In particular embodiments, the solvent used in the step of diluting may be a water based buffer fluid. In particular embodiments, the water based buffer fluid may have a pH ranging from pH 2 to 12, or 5 to 9, or around 7.

In embodiments of the present invention, the step ii. of desalting the sample comprises, consist essentially of, or consists of, a step of performing electrodialysis. The advantage linked to the use of electrodialysis is that the sample is desalted without being diluted. Furthermore, the desalting step may be done on the affinity probes and the transducer, before the measurement is started, or during measurement.

In embodiments, the method according to the invention is such that the analyte is a biomolecule, a protein, an antibody, an antigen, a biomarker, a cytokine, a nucleic acid, a small molecule (a small molecule typically having a molecular weight lower than a few kiloDaltons, for instance lower than 10 kDa, e.g. lower than 5 kDa, e.g. lower than 2 kDa, such as for instance between 50 Da and 1 kDa), or a metabolite.

Particular and preferred aspects of the invention are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of faster, more sensitive, more efficient, stable and reliable devices of this nature.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
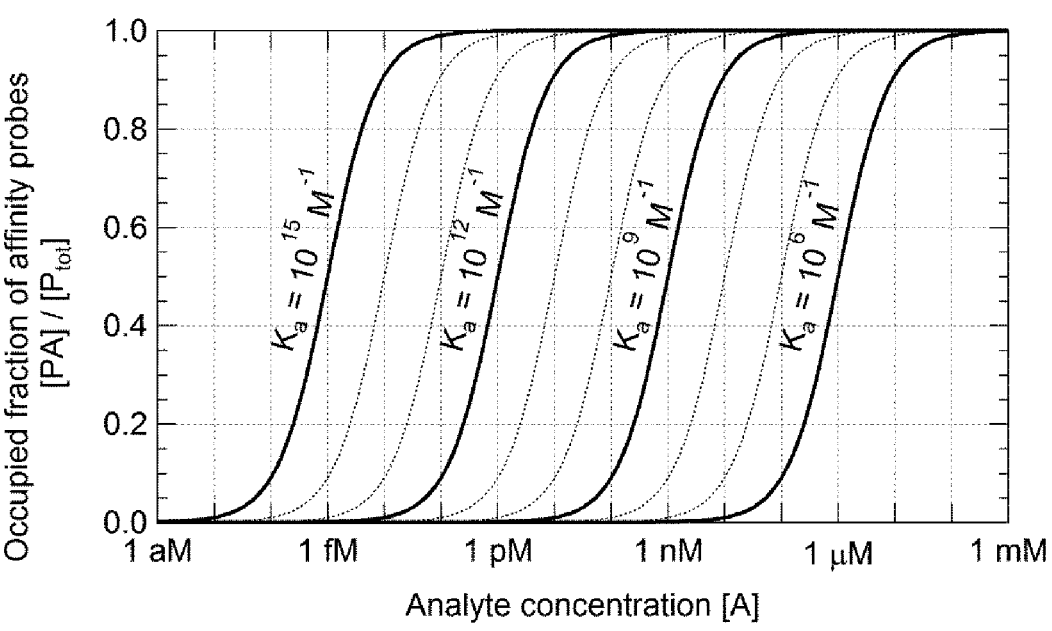
FIG. 1 is a graph of the occupied fraction, at equilibrium, of the capture probes $[PA]/[P_{tot}]$ versus the analyte concentration $[A]$ for different affinity constants, $K_a$.

In the different figures, the same reference signs refer to the same or analogous elements.

DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "coupled", should not be interpreted as being restricted to direct connections only. The terms "coupled" and "connected", along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function, such as for instance a microfluidics system. Thus, a processor with the necessary instructions for carrying out such a method or element of a method, e.g. a controller that actuates valves, mixers, etc., forms a means for carrying out the method or element of the method. Alternatively or on top thereof, a capillary circuit with liquid delay lines to perform a particular sequence of sample loading, mixing, moving to the affinity probes and the transducer, etc. also forms a means for carrying out the method or element of the method. Furthermore, the means of carrying out the function are not limited to capillary circuits, and any element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The invention will now be described by a detailed description of several embodiments of the invention. It is clear that other embodiments of the invention can be configured according to the knowledge of persons skilled in the art without departing from the true spirit or technical teaching of the invention, the invention being limited only by the terms of the appended claims.

As used herein and unless provided otherwise, the term "analyte", indicated by A in the description, refers to the substance to be measured, the substance having or not having a biological origin. By the expression "substance having a biological origin", we intend to mean a substance that is present or produced in a living organism. Particularly, the substance may be a biomolecule. For instance, the analyte may be a protein, an antibody, an antigen, a biomarker, a cytokine, a polysaccharide, a lipid, a nucleic acid, a small molecule, or a metabolite, the small molecules typically having a molecular weight lower than a few kiloDaltons, for instance lower than 10 kDa, such as lower than 5 kDa, or lower than 2 kDa, e.g. between 50 Da and 1 kDa, such as primary metabolites, secondary metabolites, and natural products.

By the term "biomolecule" is meant any molecule that is present in living organisms, including large macromolecules such as proteins, polysaccharides, lipids, and nucleic acids, as well as small molecules. The term "biomolecule" also encompasses molecules with similar properties and/or structure and/or composition, but that have been manufactured artificially rather than in a living organism.

As used herein, the term "sample" means the liquid, e.g. an aqueous solution, also called container liquid, in which it is desired to detect the presence and/or concentration of an analyte. This sample can be an original patient sample, like a quantity of blood, plasma saliva, urine, sperm; the original sample after desalting, e.g. after diluting; or the original or desalted sample to which one or more steps have been applied, which are typically done by a person skilled in the art of assay, e.g. with the intention to associate a label with an analyte, for instance by direct labelling of the analyte, by having the analyte compete with a labelled species, or by quenching a label.

The term "affinity probe", indicated by P in the description, refers to the substance having a certain affinity, e.g. a natural attraction or preferential binding, to the analyte, the substance having or not having a biological origin. By the expression "substance having a biological origin", we intend to mean a substance that is present or produced in a living organism, or has similar properties and/or structure and/or composition. For instance, the affinity probe may be an antibody, an antigen, an enzyme, a receptor, an aptamer, a nucleic acid aptamer, a peptide aptamer, or a molecularly imprinted polymer (MIP). Although we list examples of affinity probes in the singular, typically there is more than one affinity probe, even many more than one affinity probe present in the system. The affinity probes may be free in solution, or they may be immobilized on a surface, or they may be immobilized in a 3D matrix such as e.g. a gel or a dextran matrix.

By the expression "affinity-based sensing device" is meant a sensor based on a hybridisation reaction between affinity probes and analyte, for instance an affinity-based biosensor.

By the expression "response time" is meant the time necessary for obtaining a signal that is large enough to allow the determination of the presence and/or the concentration of the analyte of interest. Actual response time values depend on the relevant concentration range of the analyte, and on the noise sources, whereby the noise occurring may depend for instance on the type of assay performed, on biological noise, on transducer noise, on data processing noise, on noise due to optical detection, etc.

By the expression "physiological conditions", we intend to mean a pH equal to about 7.4 and an ionic strength equal to about 0.15 M or about 150 mM.

The term "transducer" in the context of the present invention refers to a means to convert the interaction of the analyte with affinity probes into a readout signal. The transducer may be, but does not need to be, an optical or an electronic device, and the readout signal may be, but does not need to be, an optical or electronic signal. In embodiments of the present invention, affinity probes may be present on or in, or they may form part of, the transducer. In particular embodiments, the transducer may be a means, such as an enzymatic reaction, which converts the interaction of the analyte with affinity probes into a visually discernible signal, for instance a colour indication of a particular colour depending on the type of analyte present in the sample. The intensity of the generated signal is related to, e.g. proportional to, such as directly or inversely proportional to, the amount of analyte bound to the affinity probes.

By the expression "sensing a characteristic of the analyte and/or a label attached to the analyte" is meant that the transducer of the device for sensing an analyte, for instance of the biosensor, detects presence, events or changes in quantities of analyte bound to affinity probes, and provides a corresponding output signal, generally as an electrical or optical signal. For example, measurements of the concentration, presence or absence of analyte can be obtained. "A characteristic of the analyte and/or a label attached to the analyte" includes any derived or indirect characteristic, or any characteristics that are the results of steps, actions or assays that result in a particular characteristic being associated with the sample. Sometimes the characteristic cannot be measured on the analyte itself, and in such cases labels may be provided, which bind to the analyte, and on which characteristics can be measured. For instance, in particular cases the analyte may not be fluorescent in itself, but fluorescent labels may be used, and the fluorescence of such labels may be detected.

In general, a sensor converts bulk concentration of an analyte to an output signal. If the sensor is an affinity-base sensor, as in the context of the present invention, the sensor includes the affinity probes and the transducer.

In an affinity-based sensing device, the detection of analytes in the sample may be performed through a hybridisation reaction between specified reactants and the analytes in the sample. The hybridisation reaction is based on the formation of a complex between at least two molecules, e.g. at least two biomolecules, e.g. the analyte and an affinity probe, which is a molecule or an entity acting as receptor, also called a capture probe, which may be immobilized on a substrate, or immobilized in a 3D matrix, or free in solution. The complex formation between the analyte (A) and the affinity probes (P) leads to a signal that is detectable, e.g. measurable by a signal measurement unit, or visually discernable.

The transducer converts concentration or density of affinity probes-analyte complexes to an output signal.

The response of the affinity-based sensing device may be limited by the rate of the hybridisation reaction. In the case of an affinity-based sensor based on the complexation reaction between affinity probes (P) such as for instance antibodies (Ab) acting as capture probes and an analyte (A) such as for instance an antigen (Ag), the hybridisation reaction is a binding reaction, e.g., but not limited thereto, a first order binding reaction based on the chemical equation (I):

$$P + A \underset{k_{off}}{\overset{k_{on}}{\rightleftharpoons}} PA \qquad \text{(I)}$$

where P represents the (empty) affinity probes (e.g., but not limited thereto, immobilized on the surface)
A represents the analyte (e.g. in the bulk of the liquid)
PA represents the complex affinity probe-analyte (e.g., but not limited thereto, on the surface)
$k_{on}$ represents the on-rate constant, also called association (or complexation) rate constant $k_a$
$k_{off}$ represents the off-rate constant, also called dissociation rate constant $k_d$;
or applied more specifically to antibody-antigen complexation:

$$Ab + Ag \underset{k_{off}}{\overset{k_{on}}{\rightleftharpoons}} AbAg$$

where Ab represents the (empty) antibodies (e.g., but not limited thereto, immobilized on the surface)
Ag represents the antigens (in the bulk of the sample)
AbAg represents the complex antibody-antigen (e.g., but not limited thereto, on the surface)

The affinity (or association constant) of the reaction, $K_a$ is given by the equation (II):

$$K_a = \frac{k_{on}}{k_{off}} \qquad (II)$$

At equilibrium, the concentrations of the various species obey the equation (III):

$$\frac{[PA]}{[P][A]} = K_a = \frac{k_{on}}{k_{off}} \qquad (III)$$

where [x] represents the concentration of x.
or applied more specifically to antibody-antigen compl-
exation:

$$\frac{[AbAg]}{[Ab][Ag]} = K_a = \frac{k_{on}}{k_{off}}$$

In the context of the present invention, "concentration" can mean either bulk concentration or surface concentration, depending on whether the reaction is taking place in the bulk of the liquid (e.g. with affinity probes in the bulk of the liquid), or on a surface (e.g. with affinity probes immobilized on a surface), respectively. Surface concentration is some-times also called surface density, and both terms are intended to be equivalent.

After reorganizing some terms in the equation (III), at equilibrium, the occupied fraction F of the available affinity probes is given by the equation (IV):

$$F = \frac{[PA]}{[P_{tot}]} = \frac{K_a[A]}{1 + K_a[A]} \qquad (IV)$$

where $[P_{tot}] = [P] + [PA]$ represents the total affinity probe
concentration (free+occupied);
or applied to antibody-antigen complexation:

$$F = \frac{[AbAg]}{[Ab_{tot}]} = \frac{K_a[Ag]}{1 + K_a[Ag]}$$

where $[Ab_{tot}] = [Ab] + [AbAg]$ represents the total antibody
concentration

If the concentration [A] of analyte in the bulk, e.g. the concentration [Ag] of antigens in the bulk, equals $1/K_a$, then 50% of the affinity probes, e.g. the antibodies, will be occupied at equilibrium. This is illustrated in FIG. 1 which shows the direct influence of the affinity, $K_a$, on the limit of detection of an affinity-based sensor. For a same transducer, the use of different biological systems, e.g. different couples of affinity probes and analytes, e.g. antibodies and antigens, with different $K_a$ values, leads to different limits of detection (LOD). It can be seen that for higher $K_a$ values a same occupied fraction of affinity probes is obtained at lower analyte concentrations; the transducer converts the occupied fraction of affinity probes into an output signal, hence a same output signal, e.g. sufficient to exceed the total system noise, may already be obtained at lower analyte concentrations.

Figure 2:
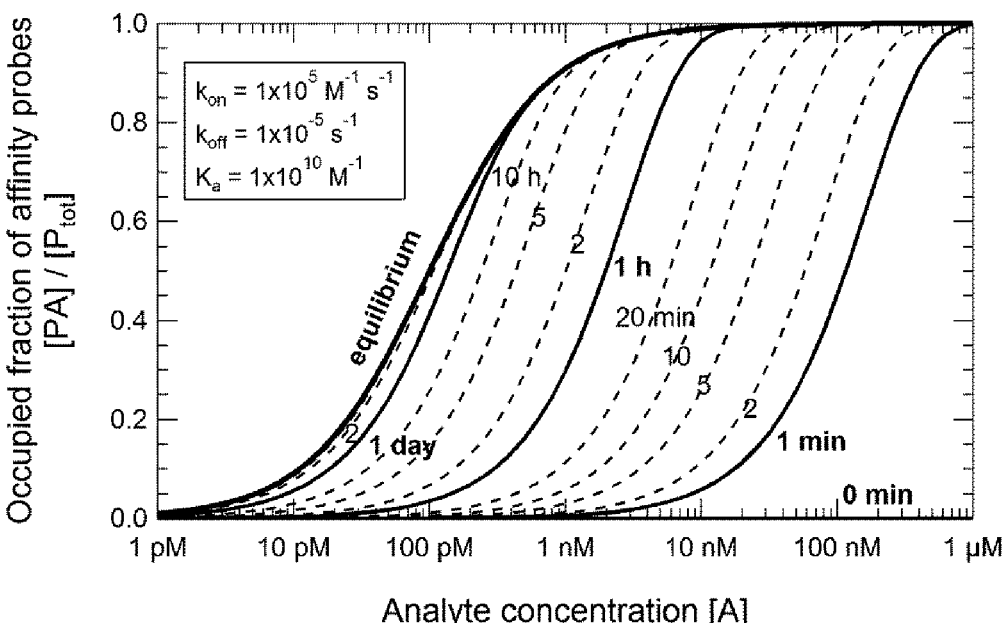
FIG. 2 is a graph of the occupied fraction of the capture probes $[PA]/[P_{tot}]$ versus the analyte concentration $[A]$, for different measurement times.

FIG. 2 illustrates a simulation of the time dependence of the signal (representative for the amount of captured analyte, e.g. antigens) as a function of the concentration of the analyte, e.g. antigen, in the example illustrated for a reaction with an on-rate constant $k_{on}$ equal to $10^5$ $M^{-1}s^{-1}$ and an off-rate constant $k_{off}$ equal to $10^{-5}$ $s^{-1}$. Despite the fact that the affinity constant, $K_a$, used in this example has been fixed as equal to $10^{10}$ $M^{-1}$, and thus the affinity probes are considered "good" affinity probes, it takes a very long time to build up the equilibrium response (e.g. in the example illustrated more than 2 days). This means that if a signal of, for instance, 0.4 is measured, the corresponding analyte concentration which can be determined therefrom depends on the time from start of the complexation reaction. Hence it is desired to have a fast complexation reaction between affinity probes and analyte, such that equilibrium is reached after only a short period of time, for instance after 10 to 15 minutes, such that a measurement signal obtained after that period of time, results in a measurement value which is representative for the actual analyte concentration (endpoint measurement), or such that the slope of the measurement signal generated by the transducer is steep (slope measure-ment).

The rate at which the hybridisation occurs is limited by $k_{on}$. For a typical macromolecular analyte having a molecu-lar weight in the range of 10 to a few 100 kDa, $k_{on}$ is in the range of $10^5$-$10^6$ $M^{-1}s^{-1}$ when both analyte, e.g. antigen, and affinity probes, e.g. antibodies, are free molecules, in other words when the affinity probes are not fixed on a surface. The limitation of the hybridisation is linked, among other, to the diffusional encounter between analyte and affinity probes, and in the majority of cases it is difficult to increase this. For surface bonded affinity probes, e.g. antibodies (Ab), the diffusional encounter rate could be even slower and thus the error in determination of analyte concentration based on a measurement value could even be higher. For example, the inventors have measured values in the range of $k_{on}=10^5$ to $3\times10^5$ $M^{-1}s^{-1}$.

The time evolution to reach the equilibrium of the chemi-cal equation (I) is given by the relation (V):

$$\frac{d[PA]}{dt} = k_{on}[P][A] - k_{off}[PA] \qquad (V)$$

wherein [A]=represents the concentration of analyte,
or applied to antibody-antigen complexation:

$$\frac{d[AbAg]}{dt} = k_{on}[Ab][Ag] - k_{off}[AbAg]$$

wherein [Ag] represents the antigen concentration
In relation (V), the concentration [A] of analyte, e.g. the concentration [Ag] of antigen, represents the concentration directly above or in contact with the affinity probes, e.g. the antibodies. In the case of a mass transport limited reaction, this concentration may drop below the bulk concentration (also known as depletion of the analyte). In this case, the concentration directly above or in contact with the affinity probes can be related to the bulk concentration by taking into account both the reaction rate, as given by relation (V) in the case of a first order affinity reaction, and the appropriate mass transport laws, e.g. diffusion equations such as Fick's law in the case of mass transport by diffusion, convection-diffusion equations in the case of mass transport by convection, where the liquid flow is treated by the appropriate fluid dynamics models, such as models based on the Navier-Stokes equations, as can be done by one of ordinary skill in the art.

The time evolution of the hybridisation reaction, e.g. of the formation of the complex between the analyte, e.g. antigen (Ag), and the affinity probes, e.g. antibodies (Ab), is given by the relation (VI):

$$\frac{[PA](t)}{[P_{tot}]} = \frac{K_a[A]}{1 + K_a[A]}\left(1 - e^{-(k_{on}[A]+k_{off})t}\right) \sim (1 - e^{-t/\tau}) \qquad \text{(VI)}$$

$$\frac{[AbAg](t)}{[Ab_{tot}]} = \frac{K_a[Ag]}{1 + K_a[Ag]}\left(1 - e^{-(k_{on}[Ag]+k_{off})t}\right) \sim (1 - e^{-t/\tau})$$

This leads to a time constant, $\tau$ $$\tau = \frac{1}{k_{on}[A] + k_{off}}$$

or applied to antibody-antigen complexation:

$$\tau = \frac{1}{k_{on}[Ag] + k_{off}} \qquad \text{(VII)}$$

Figure 4:
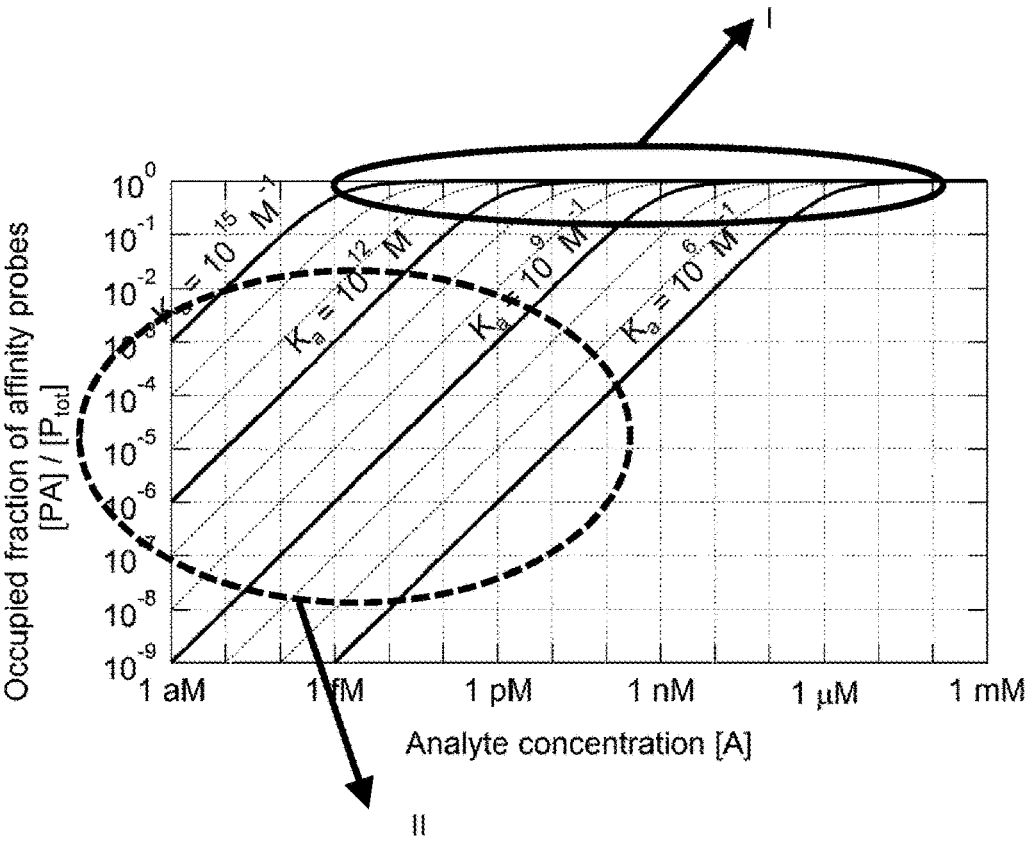
FIG. 4 is a graph of the occupied fraction, at equilibrium, of the capture probes $[PA]/[P_{tot}]$ versus the analyte concentration $[A]$ for different affinity constants, $K_a$.

FIG. 4 illustrates a simulation of the occupied fraction $[PA]/[P_{tot}]$ at equilibrium, e.g. $[AbAg]/[Ab_{tot}]$ at equilibrium as a function of the analyte concentration $[A]$ (e.g. the antigen concentration) in the sample for different affinity constants. This is the same as FIG. 1, but with a logarithmic scale instead of a linear scale on the vertical axis. Area I corresponds to situation of saturation at equilibrium, where the equilibrium situation consists of essentially 100% complexation of the affinity probes P, e.g. antibodies Ab, by the analyte A, e.g. antigen Ag, has taken place, or in other words $[PA]\approx[A_{tot}]$. In this situation $[A]>>1/K_a$, e.g. $[Ag]>>1/K_a$, leading to a time constant $\tau$, that can be approximated by the relation (VIII):

$$\tau = \frac{1}{k_{on}[A]} \qquad \text{(VIII)}$$

or applied to antibody-antigen complexation:

$$\tau = \frac{1}{k_{on}[Ag]}$$

Area II corresponds to a situation where at equilibrium less than 50% of the affinity probes P, e.g. antibodies Ab, are complexed by the analyte A, e.g. antigens Ag. In this situation $[A]<<1/K_a$, e.g. $[Ag]<<1/K_a$, leading to a time constant $\tau$, that can be approximated by the relation (IX):

$$\tau = \frac{1}{k_{off}} \qquad \text{(IX)}$$

Hence it can be seen that area I and area II indicate different simplified expressions for the time constant.

From FIG. 2 and the relations given here above, the inventors have found that analyte concentration measurements require a long measurement time. For measurements performed at short measurement times, the signal has had no time to build up, leading to the determination of erroneous analyte concentration values, or, if the considerations leading to FIG. 2 are taken into account, to smaller signals, which results in a lower signal-to-noise ratio and a lower accuracy of the measurement result. In short measurement times, the response of the sensor is thus determined by the complexation rate constant, $k_{on}$, of the hybridisation reaction (I).

It is therefore a solution provided by embodiments of the present invention to increase the association kinetics (represented by $k_{on}$) of the hybridisation reaction, to build up the signals more quickly and to reach lower (=better) limit of detection. The dissociation times of the complex (e.g. AbAg) typically are in the range of hours or days, so that the dissociation reaction can be neglected on the desired time scale of the measurement (e.g. less than 20 minutes, such as for instance around 10 min and even less) and mainly the complexation rate constant, $k_{on}$, is important.

The inventors have surprisingly found that the hybridisation rate for some affinity probe-analyte (e.g. antibody-antigen) combinations is not constant, and that the hybridisation may be highly speeded up by decreasing the ionic strength of the analyte. The inventors have found that a reduction of the ionic strength by 1 order of magnitude, for example from 100 to 10 mM, resulted in 4 or 5 orders of magnitude increasing of the complexation rate constant, $k_{on}$, and thus to a decreasing of the LOD and/or of the response time.

The reduction of the ionic strength, in accordance with embodiments of the present invention, is performed by using a device for sensing an analyte comprising a desalting unit.

Figure 5:
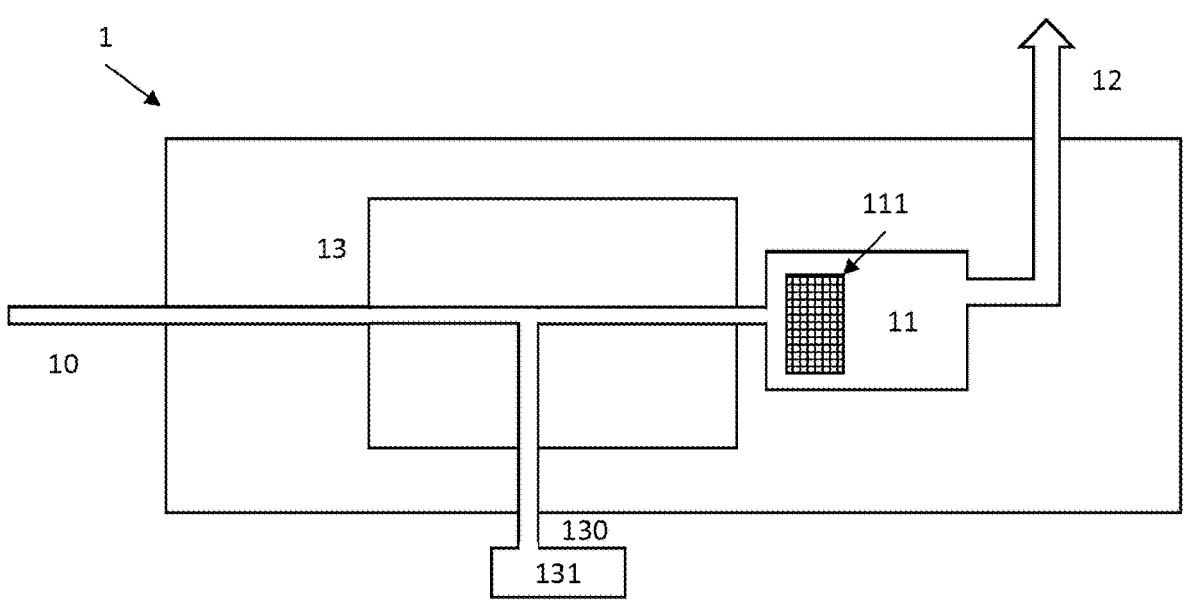
FIG. 5 is a schematic representation of a device for sensing an analyte according to embodiments of the present invention.

FIG. 5 illustrates an embodiment of a device (1) for sensing an analyte according to embodiments of the present invention. The device (1) for sensing an analyte, for instance, but not limited thereto, a biosensor, comprises at least a sample inlet (10) for receiving a sample, affinity probes (111) selected so as to have a preferential binding to the analyte, a transducer (11) for sensing a characteristic of the analyte and/or a label attached to the analyte, the transducer being not a FET transducer, and a desalting unit (13). The transducer (11) is sensitive to a characteristic of the analyte and/or a label attached to the analyte and converts an interaction of the analyte with the affinity probes (111) into a measurable signal (12), e.g. the output signal. This output signal may for instance be an electrical signal, an optical signal, or a visual signal.

The desalting unit (13) may be any suitable device for desalting the analyte. This may for instance be performed by diluting the analyte, or by extracting salt from the analyte. In embodiments of the present invention, the desalting unit (13) may comprise a port (130) and a buffer fluid reservoir (131). The buffer fluid reservoir (131) may for instance be any of an ampoule, a syringe, a blister, a well, a tube, an Eppendorf tube, a channel, or an on-chip reservoir. In particularly advantageous embodiments, the buffer fluid reservoir is a blister pack, a channel, or an on-chip reservoir.

The device (1) may be implemented with discrete components, or as an integrated chip. In the latter case, desalting may be performed off-chip, or on-chip.

The sample received at the sample inlet (10) and a stream of buffer fluid may be flown together in the desalting unit (13), and may be led to the affinity probes (111) linked to the transducer (11) as illustrated in FIG. 5, for instance by capillary forces. Alternatively, pumps may be provided to pump the sample and the buffer fluid together towards the affinity probes (111) and the transducer (11).

Figure 6:
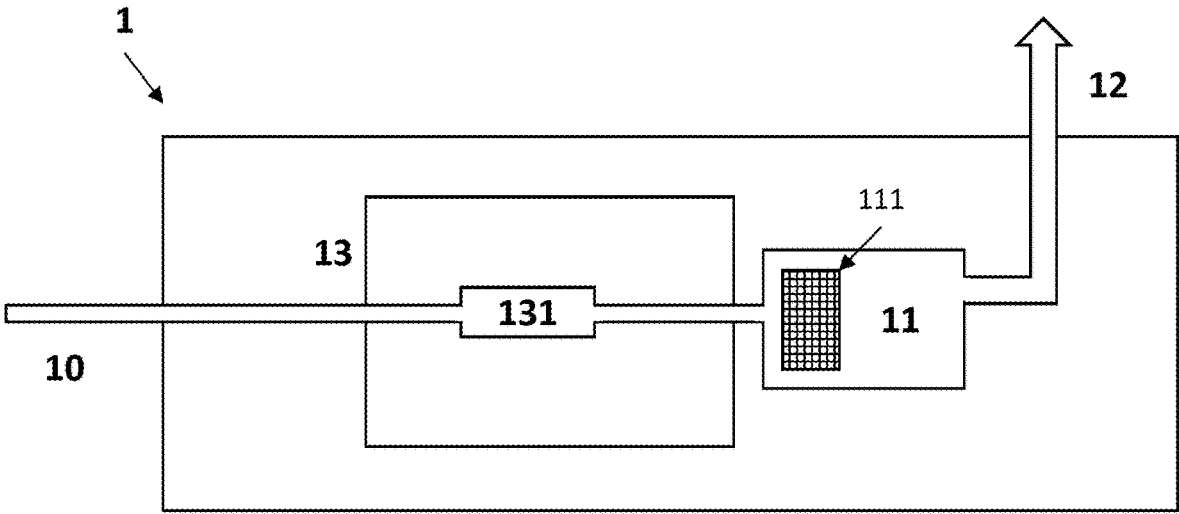
FIG. 6 is a schematic representation of a device for sensing an analyte according to alternative embodiments of the present invention.

In alternative embodiments, the sample received at sample inlet (10) may be led through a buffer fluid reservoir (131) comprising buffer fluid, such that the dilution is performed automatically, such as for instance illustrated in FIG. 6. Also in this embodiment, the flow of the sample through the buffer fluid reservoir (131) may be driven by capillary forces, or by external driving means such as pumps, for pumping sample towards the fluid reservoir (131), and for pumping a mix of sample and buffer fluid towards the affinity probes (111) and the transducer (11).

In embodiments of the present invention, the desalting may be performed when or while the analyte is associated with a label. The type of association with a label is irrelevant for embodiments of the present invention; it may include for instance direct labelling of the analyte, having the analyte compete with a labelled species, or by quenching a label. This can be done by adding a low-ionic strength buffer or solvent to the labelled sample mix. Alternatively, this can be done by preparing the label solution at low ionic strength, and mixing it in a suitable ratio with the sample. After the desalting step, the low ionic strength labelled sample may be sent over affinity probes where the hybridisation reaction relevant for the present invention takes place.

In embodiments of the present invention, labelling the analyte may take place at normal (e.g. physiological) ionic strength, and then the ionic strength may be reduced before sending the labelled analyte over the affinity probes. This has the advantage that the kinetics of premixing in the bulk are somewhat better than the kinetics of capturing the analyte or analyte complex on the surface, so slow kinetics for the bulk premixing is less critical. Furthermore, the off-rate constant $k_{off}$ is less affected by the reduced ionic strength, so once the analyte-affinity probe complex has been formed, it remains stable also at reduced ionic strength.

In embodiments of the present invention, labelling the analyte may take place after the analyte has been sent over the affinity probes. This can e.g. be done by sending a second solution containing second affinity probes over the surface with the captured analytes, the second affinity probes being labelled and also having an affinity for the analyte. In embodiments of the present invention, the second solution can be at physiological ionic strength. The second affinity probes may be provided at high concentration such that the kinetics is fast. Alternatively, the second solution can be at low ionic strength, to speed up also this interaction.

In particular embodiments, the desalting unit (13) may comprise a mixer (132) for mixing received sample with buffer fluid. The mixer may for instance be any of a microfluidic mixer, a vortex mixer, a shaker, a magnetic mixer, an ultrasonic mixer, a mechanical mixer or a rapid-mixing apparatus. The rapid mixing-apparatus may comprise two syringes, one for the delivery of a sample through the sample inlet and one for the delivery of a buffer fluid through a buffer fluid inlet and a mixing chamber.

The transducer (11) may be an optical transducer such as for instance, the present invention, however, not being limited thereto, a luminescence transducer, such as a fluorescence transducer, a total internal reflection fluorescence (TIRF) transducer, an evanescent field based fluorescence transducer, a phosphorescence transducer, a chemilumines-cence transducer, a bioluminescence transducer; a refractive index transducer, such as a Surface Plasmon Resonance (SPR) transducer, a Biolayer interferometry/reflectance interference spectroscopy (BLI/RIfS) transducer, a Photonic ring resonator, an Optical interferometer (MZI, Young); an absorbance transducer (also known as colorimetric trans-ducer); and Photonic crystals. Alternatively, the transducer may be of a non-optical type. Examples thereof, without being limiting for the present invention, are for instance an electrical transducer other than a FET-transducer, e.g. an amperometric transducer, a capacitive transducer, an elec-trical impedance transducer, an electrochemical transducer, an electrocatalytic transducer; a mechanical transducer, such as a quartz crystal microbalance (QCM), a micro-electro-mechanical system (MEMS), a nano-electromechanical sys-tem (NEMS), a microcantilever, a suspended microchannel resonator; a magnetic transducer, such as a magnetometer, a Hall effect transducer, a spin valve, a magnetic tunnel junction, a transducer based on nitrogen-vacancy (NV) centers in diamond; or a radioactivity transducer.

Figure 7:
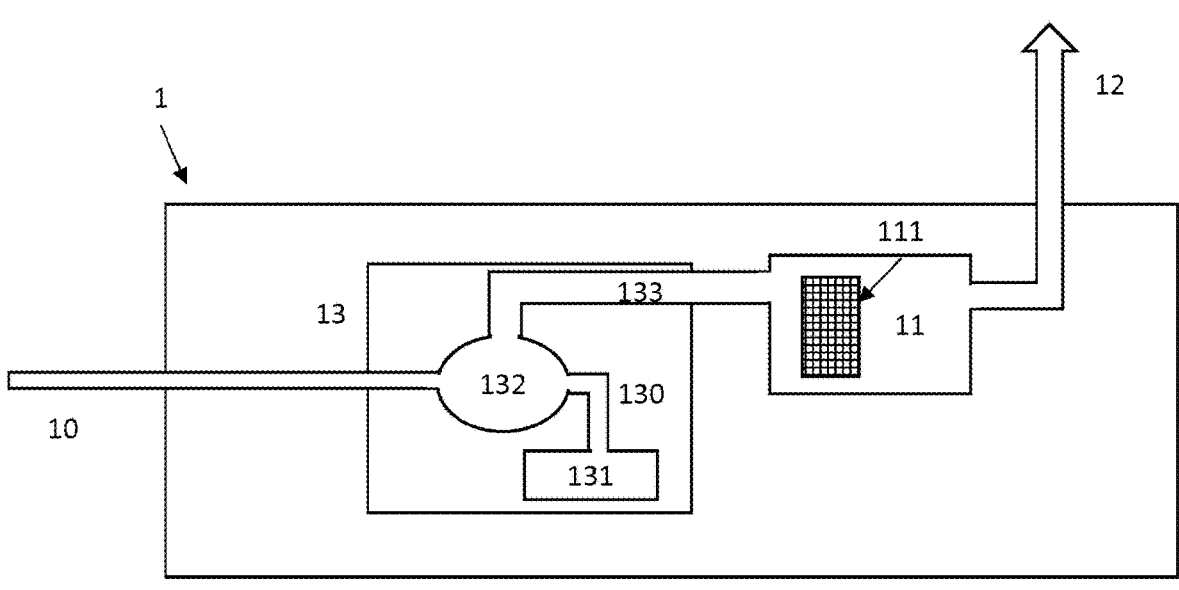
FIG. 7 is a schematic illustration of another embodiment of a device for sensing an analyte according to the present invention.

FIG. 7 illustrates a device (1) for sensing an analyte according to embodiments of the invention, wherein the desalting unit (13) comprises a mixer (132). A separate buffer fluid reservoir (131) is provided, and both sample obtained from the sample inlet (10) and buffer fluid from the reservoir (131) are led to the mixer (132), for instance by capillary forces or under influence of pumps or the like. The device (1) for sensing an analyte, for instance, but not limited thereto, a biosensor, comprises a transferring means (133) permitting the transfer of the desalted sample from the mixer (132) to the affinity probes (111) and the transducer (11). This transfer may take place by capillary forces or under influence of pumps or the like.

Figure 8:
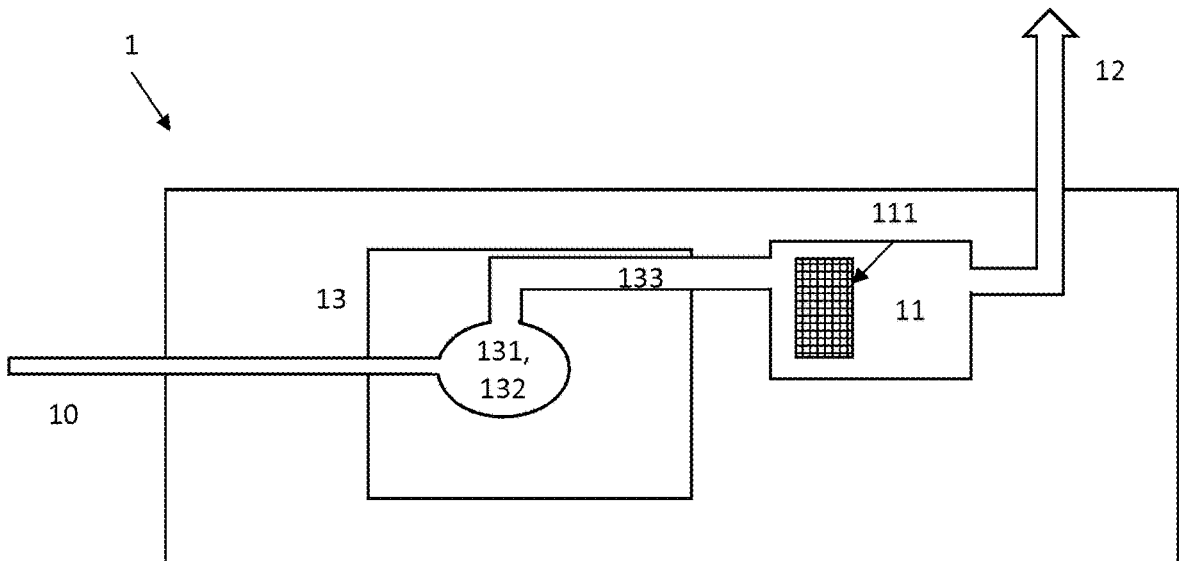
FIG. 8, FIG. 9, FIG. 10 and FIG. 11 are schematic illustrations of yet other embodiments of a device for sensing an analyte according to the present invention.

FIG. 8 illustrates an alternative device (1) for sensing an analyte according to embodiments of the invention, wherein the reservoir (131) and the mixer (132) are implemented as a single entity, i.e. the mixer is provided in the reservoir (131). Sample obtained from the sample inlet (10) is led to the reservoir (131), where it is mixed with the buffer fluid, after which the mix is led to the affinity probes (111) and the transducer (11). Transport of sample (from sample inlet to reservoir/mixer) and sample mixed with buffer fluid (from reservoir/mixer to transducer) may take place under capil-lary forces, or driven by pumps or the like. The embodiment illustrated in FIG. 8 is similar to the embodiment illustrated in FIG. 5, except that in the embodiment of FIG. 8 mixing means are provided in the reservoir (131), which is not the case in the embodiment of FIG. 5. The mixing means may be active mixing means (comprising a mechanical actuator such as a magnetic stirrer, a vortex mixer or any other suitable mixing device) or passive mixing means (not com-prising any moving parts, but modifying the flow to enhance the mixing efficiency; e.g. by creating turbulent flow, by modifying laminar flow, by increasing the residence time).

Figure 9:
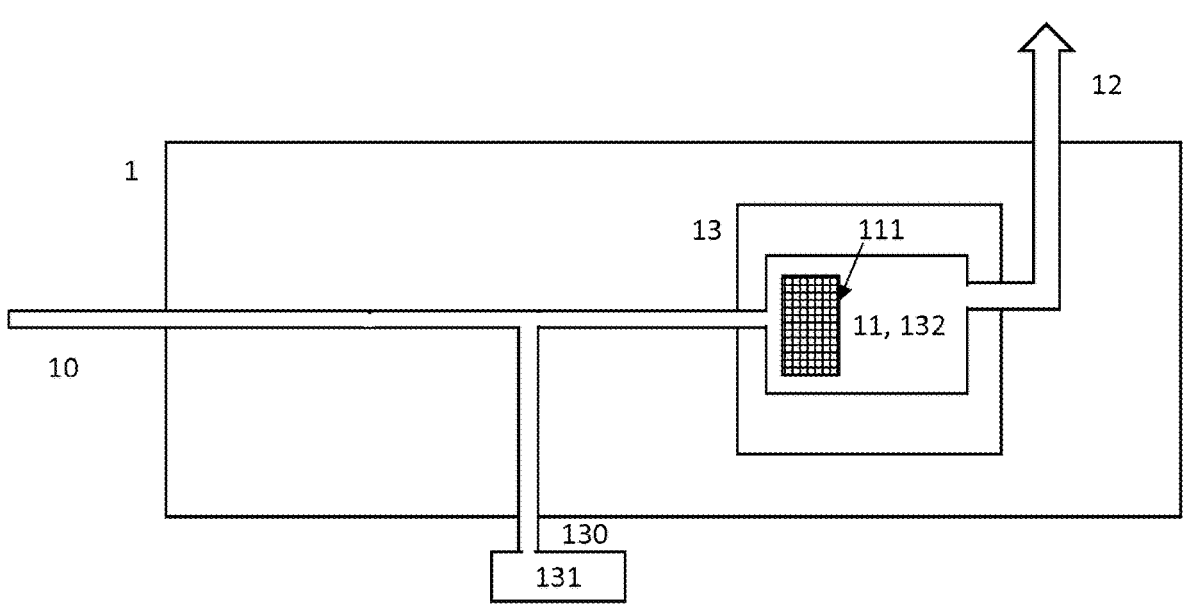

FIG. 9 illustrates another embodiment of a device (1) according to the present invention, wherein sample obtained from a sample inlet (10), and buffer fluid obtained from a reservoir (131) are flown together towards affinity probes (111) and a transducer (11) on top of which mixing means (132) are provided for better mixing the sample and the buffer fluid. The transport of fluids through the device (1) may be provided by capillary forces, or may be driven by pumps or similar.

Figure 10:
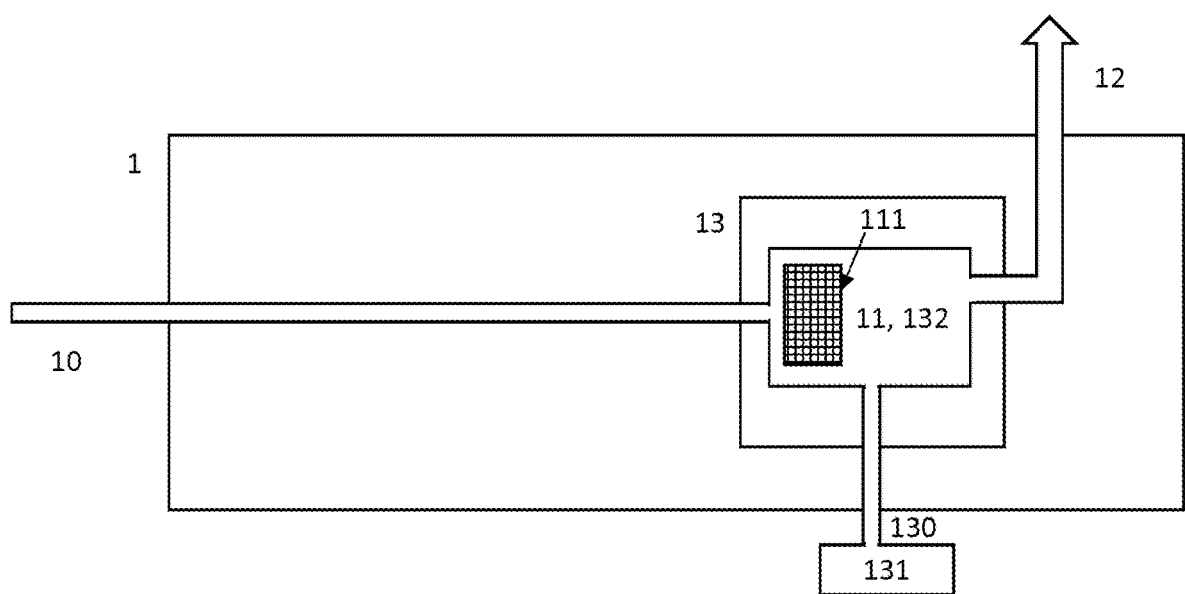

In yet alternative embodiments, as for instance illustrated in FIG. 10, essentially the same process as illustrated in FIG. 9 takes place, but instead of first flowing together the sample and the buffer fluid, and flowing these together towards the affinity probes (111) and the transducer (11), in this embodi-ment sample and buffer fluid are each flown separately, under capillary forces or driven by pumps or similar devices, towards the affinity probes (111) and the transducer (11), where they are mixed by means of a mixing means (132).

Figure 11:
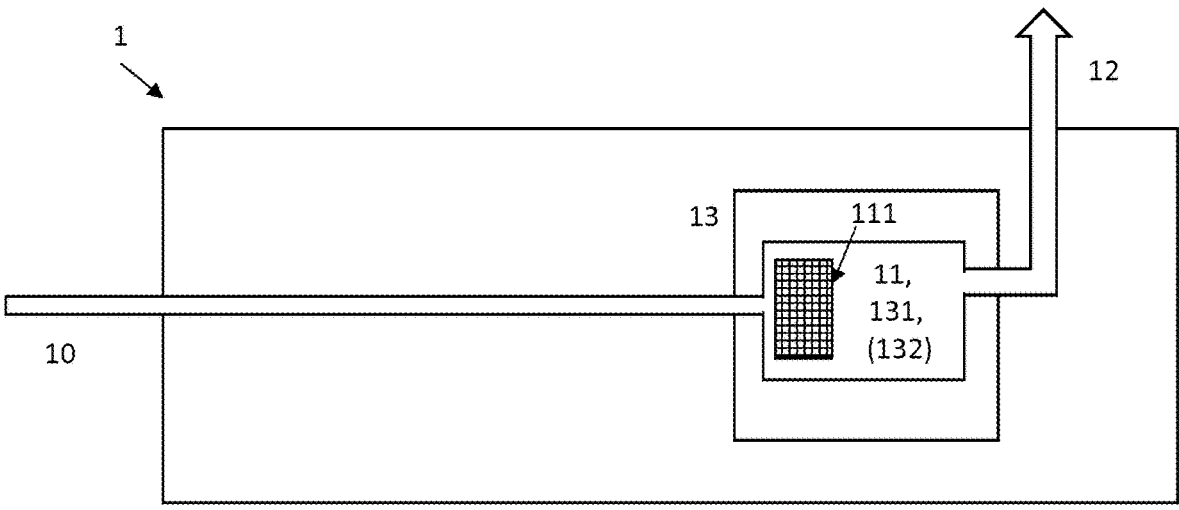

In still another embodiments, as illustrated in FIG. 11, a fluid reservoir (131) is provided on the affinity probes (111) and the transducer (11), optionally with a mixer (132) being provided in the fluid reservoir (131), and sample obtained from the sample inlet (10) is flown towards and into the fluid reservoir (131), where it is desalted, before or during the binding to the affinity probes (111) and the measurement by the transducer (11) takes place.

Figure 12:
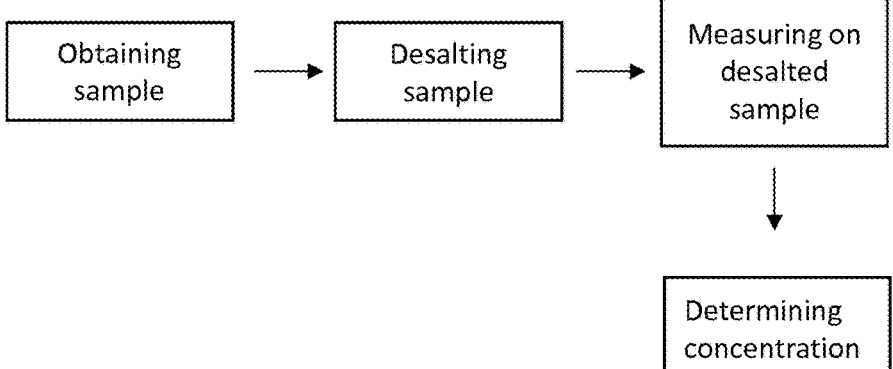
FIG. 12 represents a diagrammatic illustration of an embodiment of the method for measuring the concentration of an analyte according to the invention.

FIG. 12 represents diagrammatically an embodiment of a method for measuring the concentration of an analyte, for instance an antigen, in a sample of analyte, according to embodiments of the invention. The method comprising the steps of:

i. obtaining a sample, for example receiving a sample in the biosensor, for example a sample taken from a patient, ii. desalting the sample, thereby obtaining a desalted sample having a ionic strength lower than the ionic strength in the original sample, for instance an ionic strength ranging from 10 nM to 150 mM, more preferably from 1 mM to 150 mM, more preferably from 10 mM to 150 mM, iii. measuring at least one signal of the desalted sample, by means of an affinity-based sensing device based on affinity probes and a transducer, the transducer not being a FET-transducer, and iv. determining the concentration of the analyte in the sample using the at least one signal.

In particular embodiments of the present invention, step ii. may be a dilution step, wherein the sample is diluted with a solvent, for instance a buffer fluid. The solvent used for the dilution may be a water based buffer fluid, for instance at a pH ranging from pH 2 to 12, or 5 to 9, or around 7.

In alternative embodiments of the present invention, the desalting step may be a step wherein the sample is provided in a reservoir with one or more, preferably at least two, semipermeable walls. The reservoir is adapted for allowing $Na^+$ ions and $Cl^-$ ions to leave the reservoir through the semipermeable wall thereof, while the remainder of the sample is kept in the reservoir. Suitably actuated electrodes may be provided for attracting the ions through the semipermeable wall. This way, the sample is desalted, without decreasing the concentration of analyte molecules in the sample.

In particular embodiments, the desalting step may be part of, e.g. integrated with, the sample collection. In alternative embodiments, the sample is collected first, and is only desalted thereafter. The desalting may take place prior to the measurement. Hereto, the desalting may take place before the sample reaches the affinity probes and the transducer, or the desalting of the sample may take place on the affinity probes and the transducer.

In particular embodiments, the desalting may take place in a separate instrument, which is for instance provided in a different enclosure, separated from the enclosure where the signal measurement takes place. Alternatively, desalting and measurement may take place within a same enclosure.

By desalting the sample to be analysed, thus reducing its ionic strength, the association kinetics of the hybridisation reaction may be increased by a significant factor, up to multiple orders of magnitude.

The measurement signal may be followed in real time, and one can monitor and use the faster and larger signal in real time, and terminate the measurement more quickly.

Figure 3:
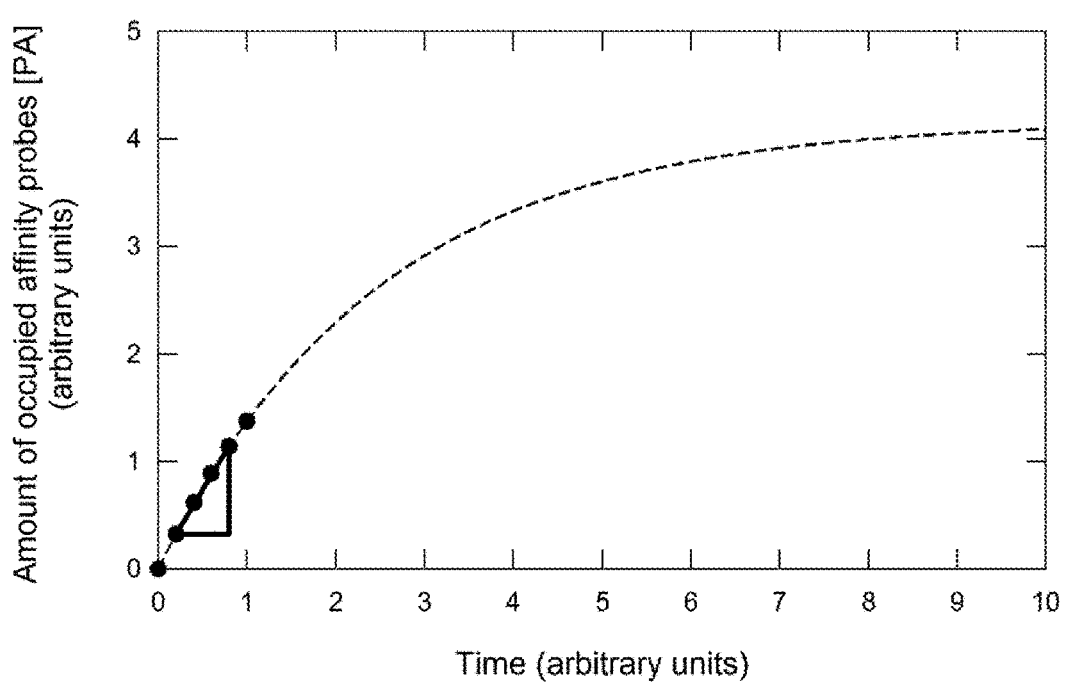
FIG. 3 is a graph of the amount of occupied capture probes $[PA]$ versus the time of an affinity-based sensing device.

FIG. 3 illustrates a measurement signal in function of time. The measurement signal, i.e. the signal generated by the affinity probes (111) and the associated transducer (11), is related to, e.g. proportional such as directly or inversely proportional to, the occupied fraction [PA] of affinity probes.

The inventors have found that a measurement of the slope of the curve of the signal may be done in order to decrease the error linked to short measurement times (less than 20 minutes, for instance less than 10 minutes) as shown on FIG. 3. Thus, embodiments of the present invention may advantageously increase the signal of the transducer, and additionally or alternatively they may reduce the response time thereof. The slope of the curve depends on the concentration of the analyte, e.g. antigen, just above the sensor surface: the more analyte is present there, the faster analyte will bind to corresponding affinity probes, hence the faster the amount of occupied affinity probes will increase, and the steeper the slope of the curve will be. Agitation may be used to avoid depletion of the analyte above the affinity probes and thus to avoid problems linked to the mass transport of the analyte, e.g. antigen.

Advantages of slope measurements are as follows. Traditionally, a particular level is measured, i.e. how large the measurement signal is at a certain point in time (called an endpoint). So a dose-response relationship is assumed. If the incubation times are long enough to reach (or approach) equilibrium, then the dose-response curves are those at equilibrium, similar to the ones shown on FIGS. 1 and 4. In this case, the exact timepoint at which the measurement is taken, is not important as the signal no longer changes with time. This is equal to what is shown far to the right on FIG. 3). However, the discussion above has shown that the required incubation times are often unreasonably long, e.g. much longer than what would be acceptable for a point-of-care (POC) application, such as for instance more than one hour, more than a couple of hours, even more than a day. For POC tests where results are desired in less than about 20 min, often in less than about 10 min, measurements are most often done when the system has not yet reached equilibrium. In this case the dose-response curves become those of FIG. 2, i.e. the response not only depends on the analyte concentration but also on the incubation time. As a result, any variation in the incubation time translates into an error on the measurement. And the shorter the incubation time, the larger the relative error on the time. This is the main uncertainty that is solved by doing a slope measurement in accordance with embodiments of the present invention.

In the initial stages of the association (complexation) reaction, the time evolution (described by equation VI) can be approximated by a linear expression. This means that the slope is independent of the exact time, as can be seen on the left-hand side of FIG. 3, and only depends on the analyte concentration (as shown by equation VI).

In addition, by continuously following the time evolution of the signal, the shape of the time-dependent curve can be reproduced, and a determination can be made as to whether it matches an expected behavior. So it can be checked whether the linear approximation of equation (VI) is still valid. If not, the full exponential dependence can be taken into account, and the full eq. VI can be used, instead of a linear approximation, to deduce the concentration.

Following the functional shape of the signal also allows to detect (and correct for) other parasitic effects. For instance in a lateral flow system, when a switch is made from buffer flow to sample flow, there may be some intermixing at the liquid front between them. This gives an error on the exact incubation time, and also an error on the slope (the slope will be smaller during this transient stage). However, in continuous measurements this can be seen, and the slope can be calculated after this transient has settled (i.e. the points affected by the transient can be discarded). As another example: if there are mass transport limitations showing up, slope measurement may allow to detect these and correct for them in the data analysis A further advantage of slope measurement is that the slope calculations can be based on many datapoints, which helps to cancel out (random) measurement errors or noise.

Yet a further advantage of slope measurement is that the measurement can be terminated as soon as a good enough signal is obtained, e.g. as soon as a required or desired accuracy is reached. This can be very fast for a sample having a high concentration of a particular biomarker, and longer for a sample where the concentration is lower, e.g. closer to the LOD. This is not possible in endpoint measurements, where the incubation times are set in advance to cover all possible conditions, hence may be unnecessarily long for certain samples.

The invention claimed is:

1. A method for measuring a concentration of an analyte in a biological sample, the method comprising:
   receiving a biological sample;
   coupling the sample to affinity probes and a transducer;
   desalting the sample, wherein desalting the sample comprises performing electrodialysis on the affinity probes and the transducer;
   measuring at least one signal of the sample by means of an affinity-based sensing device based on the affinity probes and the transducer, the transducer not being a Field Effect Transistor transducer; and
   determining the concentration of the analyte in the sample using the at least one signal.

2. The method according to claim 1, wherein desalting the sample comprises bringing the sample to an ionic strength ranging from 10 nM to 150 mM.

3. The method according to claim 1, wherein desalting the sample and measuring the at least one signal of the sample are performed simultaneously.

4. The method according to claim 1, wherein the method further comprises a step of comparing the at least one signal to a reference signal obtained with a standard solution.

5. The method according to claim 1, wherein measuring the at least one signal of the sample is performed over time to obtain a measurement curve.

6. The method according to claim 5, further comprising determining a slope of the measurement curve.

7. The method according to claim 1, wherein performing electrodialysis comprises using at least two ion-selective membranes to reduce an ionic strength of the sample.

8. The method according to claim 1, wherein desalting the sample comprises bringing the sample to an ionic strength ranging from 10 mM to 150 mM.

9. The method according to claim 1, wherein the affinity-based sensing device comprises:
   at least a sample inlet for receiving the sample;
   the affinity probes, wherein the affinity probes are selected so as to have a preferential binding to the analyte;
   the transducer, wherein the transducer is sensitive to a characteristic of the analyte and/or a label attached to the analyte and adapted to convert an interaction of the analyte with the affinity probes into a readout signal, the transducer not being a Field Effect Transistor transducer; and
   a desalting unit for desalting the received sample so as to reduce a response time and/or increase the signal of the transducer.

10. The method according to claim 1, wherein the step of desalting the sample increases association kinetics of a hybridization reaction by at least an order of magnitude.

11. The method according to claim 1, wherein desalting the sample comprises using a desalting unit, wherein the desalting unit is integrated on a same substrate as the transducer.

12. The method according to claim 1, wherein the transducer comprises an optical transducer or an electrical transducer.

\* \* \* \* \*